United States Patent
Zhi et al.

(10) Patent No.: US 11,992,621 B2
(45) Date of Patent: May 28, 2024

(54) RESPIRATOR SYSTEM

(71) Applicant: BMC MEDICAL CO., LTD., Beijing (CN)

(72) Inventors: Jianxin Zhi, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 1028 days.

(21) Appl. No.: 16/770,444

(22) PCT Filed: Dec. 10, 2018

(86) PCT No.: PCT/CN2018/120005
§ 371 (c)(1),
(2) Date: Jun. 5, 2020

(87) PCT Pub. No.: WO2019/114640
PCT Pub. Date: Jun. 20, 2019

(65) Prior Publication Data
US 2020/0368484 A1    Nov. 26, 2020

(30) Foreign Application Priority Data

Dec. 13, 2017  (CN) .......................... 201711330086.4

(51) Int. Cl.
*A61M 16/16* (2006.01)
*A61M 16/08* (2006.01)

(52) U.S. Cl.
CPC ........ *A61M 16/16* (2013.01); *A61M 16/0816* (2013.01)

(58) Field of Classification Search
CPC .. A61M 16/00; A61M 16/16; A61M 16/0816; A61M 16/0666; A61M 16/0875;
(Continued)

(56) References Cited

U.S. PATENT DOCUMENTS

| 4,676,237 A * | 6/1987 | Wood ................... A61M 16/16 261/130 |
| 7,111,624 B2 | 9/2006 | Thudor et al. |

(Continued)

FOREIGN PATENT DOCUMENTS

| CN | 203852684 U | 10/2014 |
| CN | 204446853 U | 7/2015 |

(Continued)

*Primary Examiner* — Michael R Reid
*Assistant Examiner* — Nathan M Le
(74) *Attorney, Agent, or Firm* — Volpe Koenig

(57) ABSTRACT

A ventilator system comprising: a ventilator having a first side provided with a first port; a humidifier having a second side engaging with the ventilator and provided with a second port; and a connection device provided on the first side of the ventilator or the second side of the humidifier and used to connect the first port of the ventilator with the second port of the humidifier. The connection device comprises: a first port, a second port and an airflow channel connecting the first port with the second port, wherein when the humidifier is separated from the ventilator, the connection device is capable of rotating from a connection position connecting the first port and the second port to a closed position for preventing foreign objects from falling into the first port and the second port. The ventilator system resolves issues of foreign objects falling into connection ports of a ventilator.

15 Claims, 4 Drawing Sheets

(58) Field of Classification Search
CPC ............ A61M 16/161; A61M 16/1045; A61M 2205/123; A61M 39/20; A61H 16/0026
See application file for complete search history.

(56) References Cited

U.S. PATENT DOCUMENTS

2007/0132117 A1\* 6/2007 Pujol .................. A61M 16/208
 261/119.1
2010/0242961 A1\* 9/2010 Mougel ............ A61M 16/1055
 128/203.16
2013/0174843 A1\* 7/2013 Smith .................. A61M 16/16
 128/203.26

FOREIGN PATENT DOCUMENTS

| CN | 204840557 U | 12/2015 |
|---|---|---|
| CN | 106362256 A | 2/2017 |
| CN | 205948157 U | 2/2017 |
| CN | 206566314 U | 10/2017 |
| CN | 107875490 A | 4/2018 |
| CN | 208611520 A2 | 3/2019 |
| EP | 1002552 A2 | 5/2000 |

\* cited by examiner

RESPIRATOR SYSTEM

CROSS REFERENCE TO RELATED APPLICATIONS

This application is a 35 USC § 371 national stage of, PCT/CN2018/120005, which was filed Dec. 10, 2018, claims priority to Chinese Application No. 201711330086.4, filed on Dec. 13, 2017, and is entitled "VENTILATOR SYSTEM," both of which are incorporated herein by reference as if fully set forth.

FIELD

The present invention relates to the field of ventilation apparatuses, in particular to a respirator system.

BACKGROUND

At present, in a respirator system, the humidifier and the host machine of respirator are connected usually by assembling them in a front-back direction or left-right direction in a horizontal plane. Such an assembling is not adaptive to narrow and small spaces. The problem of large space occupation can be solved effectively if the respirator and the humidifier are connected by assembling them in a top-bottom direction. However, to assemble the respirator and the humidifier from top to bottom, the ventilation port of the host machine of the respirator or the ventilation port of the humidifier should be open upward or upward obliquely; after the humidifier is taken out, foreign objects may easily fall into the host machine or the humidifier through the ventilation port that is open upward.

Therefore, it is desirable to develop a novel respirator system, in which the humidifier and the host machine of respirator can be assembled to each other while falling of foreign objects into the host machine of respirator or humidifier can be prevented.

SUMMARY

The object of the present invention is to solve the problem that foreign objects may easily fall into the ventilation ports that are open upward or upward obliquely on existing host machine of respirators or humidifiers in the prior art.

To solve the above-mentioned technical problem, the present invention provides a respirator system, which comprises a host machine of respirator having a first connect port; a humidifier having a second connect port in communication with the first connect port; and a connection device provided on the host machine of respirator or the humidifier and configured to communicate the first connect port of the host machine of respirator with the second connect port of the humidifier, and comprising a first port, a second port and an airflow channel communicating the first port with the second port; wherein when the humidifier is separated from the host machine of respirator, the connection device is capable of rotating from a connection position communicating the first connect port and the second connect port to a rest position for preventing foreign objects from falling into the first port and second port.

With the technical scheme in the present invention, the host machine of respirator and the humidifier communicate with each other by means of the connection device; when the respirator is separated from the humidifier, the connection device is capable of rotating to a rest position so that intrusion of foreign objects into the first port and the second port can be prevented. Thus, when the host machine of respirator and the humidifier are separated from each other, the connection device is in the rest position and can prevent intrusion of foreign objects into the respirator system.

Preferably, the host machine of respirator has a first side on which the first connect port is provided; the humidifier has a second side which is in fit with the first side and on which the second connect port is provided;

Preferably, the rest position is a position where the first port and/or the second port is in a horizontal position, or in a vertically downward-facing position, or in any inclined position between the horizontal position and the vertically downward-facing position, so as to prevent foreign objects from falling into the connection device.

Preferably, the respirator system comprises an elastic member provided between the first side and the connection device and configured to reset the connection device from the connection position to the rest position. The elastic member keeps the connection device in the rest position when the host machine of respirator is not assembled with the humidifier. Moreover, when the humidifier is separated from the host machine of respirator, the elastic member can drive the connection device to rotate, so that the connection device automatic resets from the connection position to the rest position.

Preferably, the connection device is hinged to the first side; a pressing member is provided on the second side and configured to press the connection device to drive the connection device to rotate from the rest position to the connection position. Thus, the connection device can rotate when the humidifier is assembled from top to bottom with respect to the host machine of respirator, so that the first port rotates and connect the second connect port of the humidifier and the second port rotates and connect the first connect port of the respirator.

Preferably, a first protrusion is provided on an end of the connection device, and the pressing member is a second protrusion capable of pressing the first protrusion to drive the connection device to rotate, so as to provide an acting moment by means of the second protrusion pressing the first protrusion.

Preferably, both the first protrusion and the second protrusion are strip members; the first protrusion is horizontal when the connection device is in the rest position; the first protrusion is vertical when the connection device is in the connection position, and thereby the second protrusion drives the connection device to rotate by pressing the first protrusion that has certain width at any position in the vertical direction.

Preferably, a notch that is recessed and penetrates downward to the bottom surface of the humidifier is formed in the second side; the notch comprises a top wall and two opposite side walls, and the second connect port is formed on the top wall of the notch; the second protrusion is formed on the two side walls and extend from top to bottom. Thus, the first side and the second side can be coupled with each other to form an internal cavity, in which the connection device rotates to communicate the first connect port with the second connect port. Thus, the space occupied by the respirator system can be further reduced.

Preferably, the connection device comprises a main body part and connecting end faces at the two ends of the main body part; a rotating shaft extending along the first side of the host machine of respirator is provided between the two connecting end faces; a shaft hole in fit with the rotating shaft is formed in the first side to ensure that the connection device can rotate.

Preferably, a recessed first slot is formed in the first side; the first slot comprises a bottom wall and four side walls, and the first connect port is formed in the bottom wall of the first slot; the shaft hole is formed in the side walls of the first slot at the two sides of the first connect port. Thus, the shaft hole can be formed conveniently without interference to the assembling and disassembling operations of the humidifier and the host machine of respirator.

Preferably, a second slot recessed with respect to the first slot is further formed in the first side; when the connection device is in the rest position, a part of the airflow channel extends out of the second slot and the second port faces downward, and the other part of the airflow channel is accommodated in the second slot. Thus, in the rest position, since the second port is open downward, intrusion of foreign objects into the host machine of respirator through the second port can be prevented.

Preferably, the airflow channel comprises a first pipe for outlet air and a second pipe for inlet air.

Preferably, the first pipe and the second pipe are curved piped aligned side by side in the circumferential direction of the rotating shaft, so that the ports of the first pipe and the second pipe can rotate around the rotating shaft when the connection device rotates.

Preferably, the first port, the second port, the first connect port and the second connect port are elastic ports. Thus, the connection device can be connected with the host machine of respirator and the humidifier elastically.

Preferably, linear sealing or face sealing or resilient sealing is formed between the first port and the first connect port or between the second port and the second connect port.

DETAILED DESCRIPTION

Figure 1:
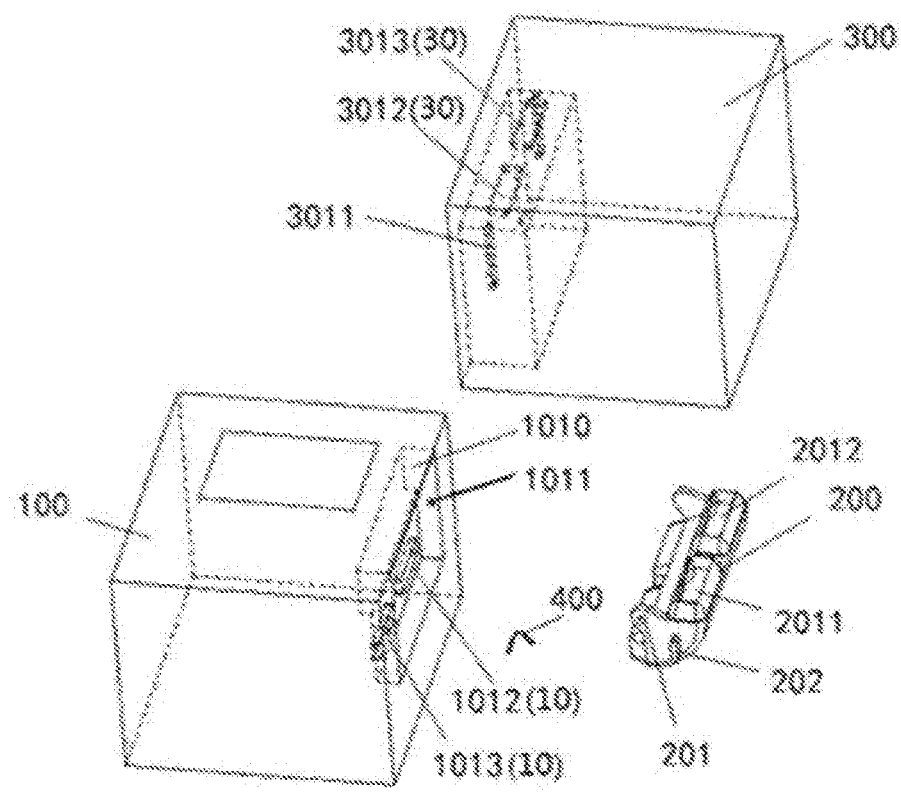
FIG. 1 is a schematic structural diagram of the respirator system according to an embodiment of present invention.

Hereunder some embodiments of the present invention will be detailed with reference to the accompanying drawings. It should be understood that the embodiments described herein are only provided to describe and explain the present invention rather than constitute any limitation to the present invention.

In the present invention, unless otherwise specified, the words that denote directions or orientations, such as "above", "below", "top", and "bottom", etc., are usually used to describe the relative position relations among the components with respect to the direction shown in the accompanying drawings or the vertical, plumb, or gravity direction; "vertical direction" refers to the up-down direction of the paper surface of the drawing; "inside" and "outside" usually refer to inside and outside of a cavity with respect to the cavity or inside and outside in the radial direction with respect to the center of a circle.

In the prior art, when the respirator and the humidifier are connected by assembling them from top to bottom, usually the ventilation port of the host machine of respirator or the ventilation port of the humidifier is configured to be open upward or upward obliquely; after the humidifier is taken out, foreign objects may easily fall into the host machine of respirator or the humidifier through the ventilation port that is open upward.

To solve the above-mentioned technical problem, the present invention provides a respirator system, which, as shown in FIG. 1, comprises: a host machine of respirator 100, a humidifier 300 and a connection device 200. The host machine of respirator 100 is configured to pressurize the air entering the host machine of respirator 100 to form pressurized air at preset pressure and discharge the pressurized air. The host machine of respirator 100 has a first connect port 10 for discharging the pressurized air. The humidifier 300 is arranged downstream from the host machine of respirator 100 and configured to introduce the pressurized air, humidify the pressurized air to form humidified and pressurized air, and discharge the air to a respiratory tube. The humidifier 300 has a second connect port 30 for introducing the pressurized air. The connection device 200 is arranged between the first connect port 10 and the second connect port 30, and may be arranged on the host machine of respirator 100 or the humidifier 300.

In a specific embodiment, the host machine of respirator 100 has a first side on which the first connect port 10 is provided; the humidifier 300 has a second side, which is in fit with the first side of the host machine of respirator 100 and on which the second connect port 30 is provided. The connection device 200 is arranged on the first side of the host machine of respirator 100 or on the second side of the humidifier 300 and is configured to communicate the first connect port 10 of the host machine of respirator 100 with the second connect port 30 of the humidifier 300. The connection device 200 may be hinged to or rotatably mounted by means of a pin shaft to the first side of the host machine of respirator 100 or the second side of the humidifier 300.

The host machine of respirator 100 or the humidifier 300 may be cuboid-shaped, cube-shaped, sphere-shaped, or hemisphere-shaped; or the host machine of respirator 100 and the humidifier 300 form a spherical structure after they are assembled, i.e., the host machine of respirator 100 and the humidifier 300 are a hemispherical or essentially hemispherical structure respectively; of course, the host machine of respirator 100 and the humidifier 300 may be shaped with a flat bottom, so that the respirator can be placed on tabletop conveniently.

The connection device 200 comprises a first port, a second port, and a airflow channel communicating the first port with the second port. When the humidifier 300 is separated from the host machine of respirator 100, the connection device 200 is capable of rotating from a connection position where the first connect port 10 is in communication with the second connect port 30 to a rest position for preventing foreign objects from falling into the first port and the second port. The host machine of respirator 100 may be communicated with the humidifier 300 by means of the connection device 200; when the host machine of respirator 100 is separated from the humidifier 300, the connection device 200 is capable of rotating to the rest position so that intrusion of foreign objects into the first port and the second port can be prevented. Thus, when the host machine of respirator 100 and the humidifier 300 are separated from each other, the connection device 200 is in the rest position, so as to prevent intrusion of foreign objects into the respirator system. When the connection device 200 is in the connection position, it is ensured that the first connect port 10 is in communication with the second connect port 30.

In the present invention, the host machine of respirator 100 and the humidifier 300 may be assembled in the top-bottom direction, and the host machine of respirator 100 and the humidifier 300 communicate with each other via the connection device 200, wherein one connect port of the first connect port 10 and the second connect port 30 may be open downward or downward obliquely; and the other connect port of the first connect port 10 and the second connect port 30 may be open upward or upward obliquely, or may be open in the horizontal direction. The connection device 200 is usually arranged above the other connect port, so that the connection device 200 may block the port of the other connect port to prevent foreign objects from falling into the other connect port even when the connection device 200 is in the rest position.

In another embodiment, the host machine of respirator 100 and the humidifier 300 may be assembled in the left-right direction, as long as the connection device 200 communicate the first connect port 10 with the second connect port 30 when the host machine of respirator 100 and the humidifier 300 are assembled; when the host machine of respirator 100 and the humidifier 300 are separated from each other, the connection device 20 is turned over so that the first port or the second port of the connection device 20 faces the interior of the installed component (the host machine of respirator 100 or the humidifier 300) or the first port or the second port of the connection device 20 faces downward or downward obliquely, so as to prevent foreign objects from entering by falling.

When the connection device 200 is in the connection position, the host machine of respirator 100 and the humidifier 300 communicate with each other via the connection device 200, i.e., the first connect port of the host machine of respirator 100 communicates with the second port of the connection device 200, and the second connect port of the humidifier 300 communicates with the first port of the connection device 200.

When the host machine of respirator 100 or the humidifier 300 is taken out (i.e., the host machine of respirator 100 and the humidifier 300 are separated from each other), the connection device 200 may rotate from the connection position to the rest position to prevent foreign objects from entering into the respirator system.

Preferably, in the rest position, the first port and/or the second port is in a horizontal position, or in a vertically downward position, or in any inclined position between the horizontal position and the vertically downward position, to prevent foreign objects from falling into the connection device 200.

The following embodiment is mainly described in an implementation that the connection device 200 is provided on the first side of the host machine of respirator 100, and may be used as a reference for the implementation that the connection device 200 is provided on the second side of the humidifier 300. There is no substantial difference between the two implementations.

To ensure that the connection device 200 is in the rest position when the host machine of respirator 100 and the humidifier 300 are not assembled together, the respirator system comprises an elastic member 400 provided between the first side and the connection device 200 and configured to reset the connection device 200 from the connection position to the rest position. Preferably, the elastic member 400 is a torsion spring. Thus, the elastic member 400 will keep the connection device 200 in the rest position when the host machine of respirator 100 and the humidifier 300 are not assembled together. Moreover, when the humidifier 300 is separated from the host machine of respirator 100, the elastic member 400 may drive the connection device 200 to rotate, so that the connection device 200 automatic resets from the connection position to the rest position.

Furthermore, the connection device 200 is hinged to the first side to ensure that the connection device 200 can rotate so that the first port connect the second connect port 30 of the humidifier 300 and the second port connect the first connect port 10 of the respirator 100 when the humidifier 300 is assembled from top to bottom with respect to the host machine of respirator 100; a pressing member is provided on the second side and configured to press the connection device 200 so that the connection device 200 rotates from the rest position to the connection position. Preferably, a first protrusion 202 is provided at an end of the connection device 200, and the pressing member is a second protrusion 3011 capable of pressing the first protrusion 202 to drive the connection device 200 to rotate.

Figure 2:
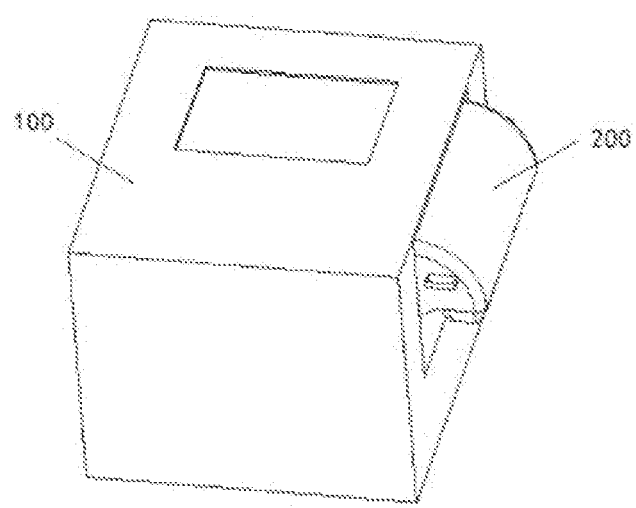
FIG. 2 is a schematic diagram illustrating the host machine of respirator and the connection device of present invention in the rest position.
Figure 5:
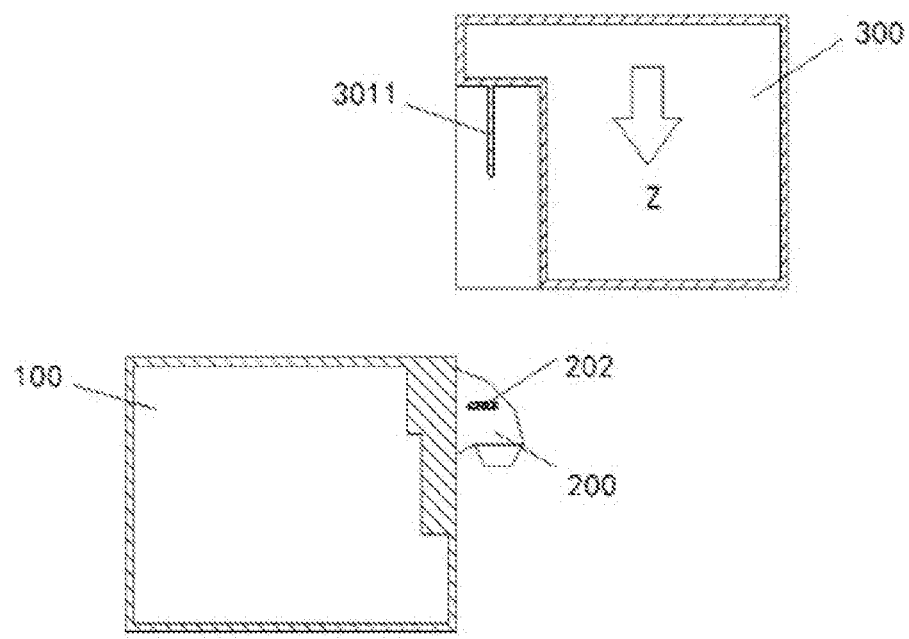
FIG. 5 is a schematic diagram illustrating the humidifier and the host machine of respirator of present invention before they are assembled.
Figure 6:
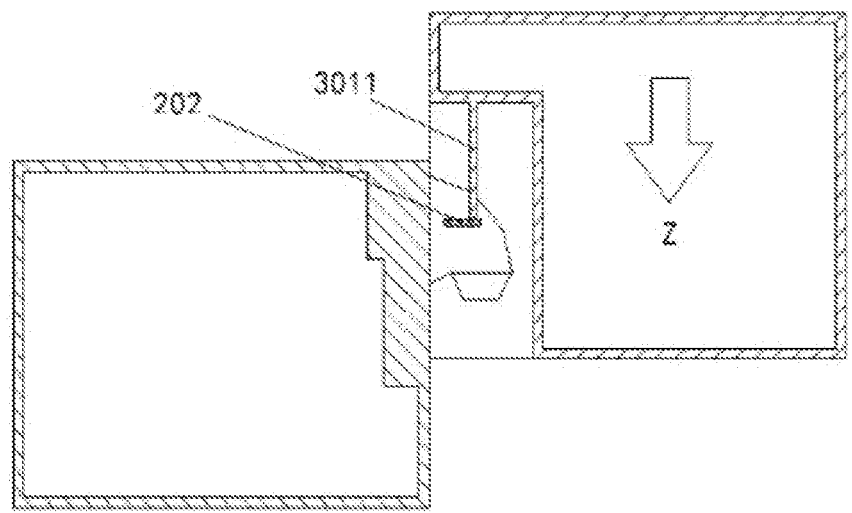
FIG. 6 is a schematic diagram illustrating the humidifier and the host machine of respirator of present invention during assembling.

The first protrusion 202 is provided at a connecting end face of the connection device 200 in an area offset from the rotating shaft 201 to ensure an effective acting moment. To ensure sufficient acting moment, the distance from the position where the second protrusion 3011 presses the first protrusion 202 to the rotating shaft 201 may be configured reasonably. Furthermore, as shown in FIG. 2, both the first protrusion 202 and the second protrusion 3011 are strip members. When the connection device 200 is in the rest position, the first protrusion 202 is horizontal. When the connection device 200 is in the connection position, the first protrusion 202 is vertical. Thus, the connection device 200 can be driven to rotate as long as the second protrusion 3011 presses the first protrusion 202 that has certain width at any position in the vertical direction. As shown in FIG. 6, the second protrusion 3011 preferably presses the first protrusion 202 in the vertical direction at a position that is farthest from the rotating shaft 201. In that case, lower force is required to overcome the elastic force of the elastic member 400 and make the second protrusion 3011 press the first protrusion 202 to drive the connection device 200 to rotate in the clockwise direction as shown in FIGS. 5-8, so that the connection device 200 rotates from the rest position to the connection position.

Figure 7:
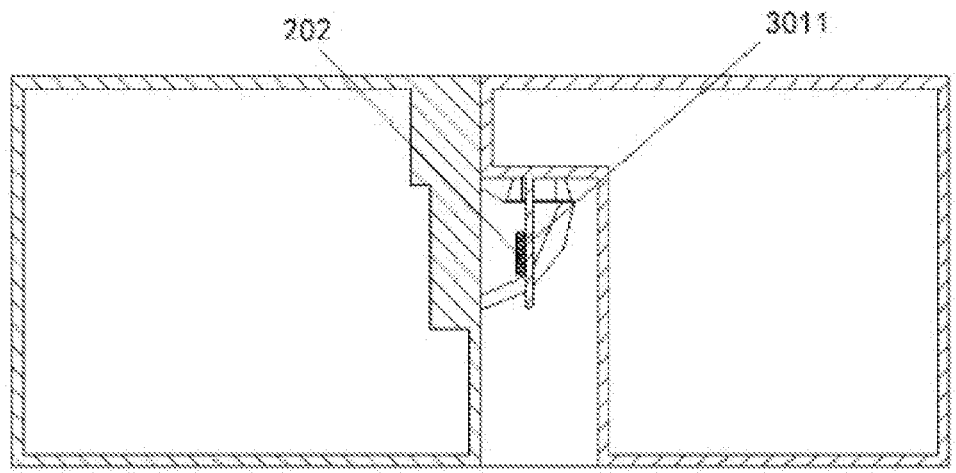
FIG. 7 is a schematic diagram illustrating the humidifier and the host machine of respirator of present invention after they are assembled.
Figure 8:
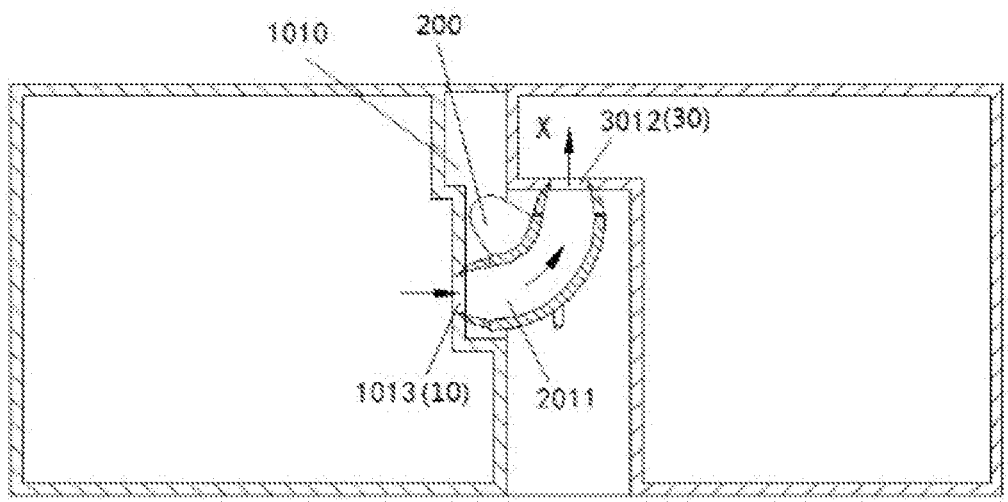
FIG. 8 is a sectional view of the structure shown in FIG. 7.

In the above embodiment, the second protrusion 3011 is strip-shaped and extends in the height direction of the humidifier 300. Preferably, the second protrusion 3011 extends from the top of the side wall to the central area of the side wall. When the humidifier 300 is assembled from top to bottom with respect to the host machine of respirator 100, as shown in FIGS. 5-7, the second protrusion 3011 firstly presses the first protrusion 202 perpendicularly; then the first protrusion 202 rotates with the connection device 200 by 90° and is parallel to the second protrusion 3011; finally, the second protrusion 3011 blocks the first protrusion 202 from the outer side of the first protrusion 202, so that the connection device 200 is kept in the connection position. More preferably, the length of the second protrusion 3011 is greater than the length of the first protrusion 202. Thus, the connection device 200 can be firmly held in the connection position, so that the first port is connected with the second connect port 30 stably, the second port is connected with the first connect port 10 stably, and thereby the host machine of respirator 100 and the humidifier 300 communicate with each other stably.

To ensure that the connection device 200 can rotate, the connection device 200 comprises a main body part and connecting end faces positioned at the two ends of the main body part; a rotating shaft 201 extends along the first side of the host machine of respirator 100 is provided between the two connecting end faces; a shaft hole 1011 fitted with the rotating shaft 201 is formed in the first side.

Furthermore, a first slot is formed recessed in the first side, so that the shaft hole 1011 can be formed conveniently without interfering the assembling and disassembling operations of the humidifier 300 and the host machine of respirator 100; the first slot comprises a bottom wall and four side walls, and the first connect port 10 is formed on the bottom wall of the first slot; the shaft hole 1011 is formed in the side walls of the first slot at the two sides of the first connect port 10.

A second slot 1010 recessed with respect to the first slot is further formed in the first side; when the connection device 200 is in the rest position, a part of the airflow channel extends out of the second slot 1010 and the second port faces downward, and the other part of the airflow channel is accommodated in the second slot 1010. Thus, in the rest position, since the second port is open downward, intrusion of foreign objects into the host machine of respirator 100 through the second port can be prevented. However, to prevent foreign objects from falling into the host machine of respirator 100 through the first port, the first port is accommodated in the second slot 1010, such that the first port abut against a side wall of the second slot 1010 in a sealed state.

A notch that is recessed and penetrates downward to the bottom surface of the humidifier 300 is arranged on the second side; the notch comprises a top wall and two opposite side walls, and the second connect port 30 is formed on the top wall of the notch; the second protrusion 3011 is formed on the two side walls and extend from top to bottom. Thus, the first side and the second side can be coupled with each other to form an internal cavity, in which the connection device 200 rotates to communicate the first connect port 10 with the second connect port 30. Thus, the space occupied by the respirator system can be further reduced.

Figure 3:
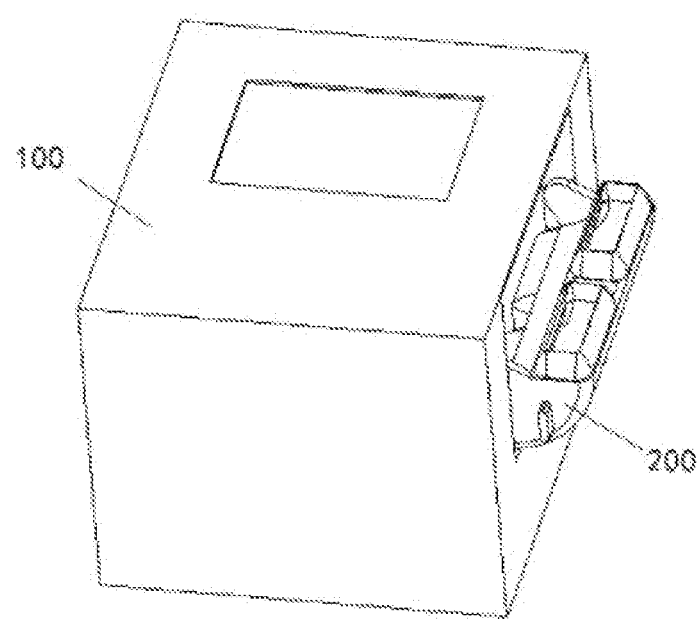
FIG. 3 is a schematic diagram illustrating the host machine of respirator and the connection device of present invention in the connection position.
Figure 4:
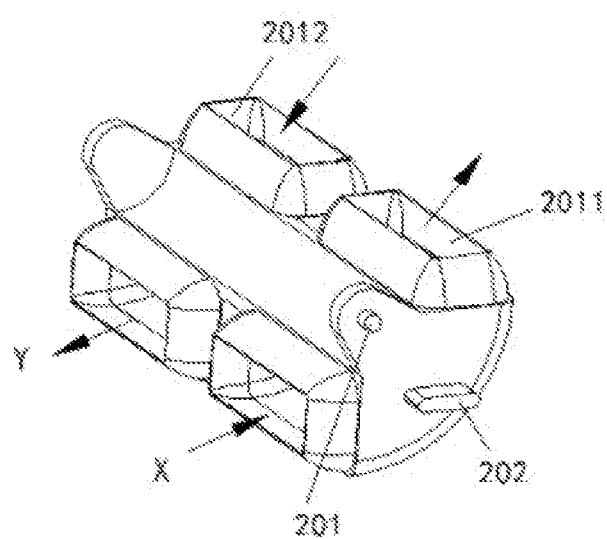
FIG. 4 is a schematic structural diagram of the connection device of present invention.

In a specific embodiment of the present invention, the airflow channel comprises a first pipe 2011 for outlet air and a second pipe 2012 for inlet air, wherein the first pipe 2011 and the second pipe 2012 communicate with the first connect port 10 and the second connect port 20, and the first connect port 10 and the second connect port 30 have an air inlet opening and an air outlet opening respectively. Specifically, the first connect port 10 comprises a respirator air inlet 1012 and a respirator air outlet 1013, the second connect port 20 comprises a humidifier air inlet 3012 and a humidifier air outlet 3013, the two ends of the first pipe 2011 are connected to the respirator air outlet 1013 and the humidifier air inlet 3012 respectively, and the two ends of the second pipe 2012 are connected to the respirator air inlet 1012 and the humidifier air outlet 3013 respectively. The first pipe 2011 and the second pipe 2012 are aligned side by side in the axial direction of the rotating shaft 201 and are both curved pipes extending along the circumference centering on the center line of the rotating shaft 201, so that the two ports of the first pipe 2011 and the second pipe 2012 can rotate around the rotating shaft when the connection device 200 rotates. The first pipe 2011 and the second pipe 2012 are in the same length, parallel to each other, and arranged surround the circumference of the rotating shaft 201. One of the ports of the first pipe 2011 and the second pipe 2012 (e.g., the port on the top in FIG. 4) is the first port, and the other of the ports of the first pipe 2011 and the second pipe 2012 (e.g., the port on the bottom in FIG. 4) is the second port. The included angle between the plane of the first port and the plane of the second port preferably is 90°. In that case, as shown in FIGS. 2 and 3, the second connect port 30 of the humidifier 300 is open downward, and the first connect port 10 of the host machine of respirator 100 is open to the humidifier 300 in the horizontal direction. When the humidifier 300 is assembled from top to bottom with respect to the host machine of respirator 100, the connection device 200 rotates by 90° in the clockwise direction, and the first port rotates from the rest position (i.e., the opening of the first port faces the interior of the host machine of respirator 100 laterally) to the connection position in which the opening faces upward. The second port rotates from the rest position (i.e., the opening faces downward) to the connection position in which the opening faces the interior of the host machine of respirator 100 laterally and connect the first connect port 10.

Preferably, one or more of the side ports of the first pipe 2011, the side ports of the second pipe 2012, the first connect port 10 and the second connect port 30 are elastic connect ports. Thus, the connection device 200 can be connected with the host machine of respirator 100 and the humidifier 300 elastically. Preferably, linear sealing, face sealing or resilient sealing is formed between the first port and the first connect port 10 or between the second port and the second connect port 30, to ensure leak tightness between the connections.

While the present invention is described above in detail in some preferred embodiments with reference to the accompanying drawings, the present invention is not limited to those embodiments. Various simple variations may be made to the technical scheme in the present invention, including combinations of the specific technical features in any appropriate form, within the scope of the technical ideal of the present invention. To avoid unnecessary repetition, the possible combinations are not described specifically in the present invention. However, such simple variations and combinations shall also be deemed as having been disclosed and falling in the scope of protection of the present invention.

The invention claimed is:

1. A respirator system, comprising:
a host machine of respirator (100) having a first connect port (10) for ventilation;
a humidifier (300) having a second connect port (30) in communication with the first connect port (10); and
a connection device (200) provided on the host machine of respirator (100) or the humidifier (300) and configured to communicate the first connect port (10) of the host machine of respirator (100) with the second connect port (30) of the humidifier (300), the connection device (200) comprises a first port, a second port and an airflow channel communicating the first port with the second port;

wherein when the humidifier (300) is separated from the host machine of respirator (100), the connection device (200) is capable of rotating from a connection position where the first connect port (10) is in communication with the second connect port (30) to a rest position for preventing foreign objects from falling into the first port and the second port.

2. The respirator system of claim 1, wherein the host machine of respirator has a first side on which the first connect port is provided; the humidifier has a second side which is fit with the first side and on which the second connect port is provided.

3. The respirator system of claim 1, wherein the rest position is a position where the first port and/or the second port is in a horizontal position, or in a vertically downward-facing position, or in any inclined position between the horizontal position and the vertically downward-facing position.

4. The respirator system of claim 2, comprising an elastic member provided between the first side and the connection device and configured to reset the connection device from the connection position to the rest position.

5. The respirator system of claim 2, wherein the connection device is hinged to the first side; a pressing member is provided on the second side and configured to press the connection device so that the connection device can rotate from the rest position to the connection position.

6. The respirator system of claim 5, wherein a first protrusion (202) is provided on an end of the connection device (200), and the pressing member is a second protrusion (3011) capable of pressing the first protrusion (202) to drive the connection device (200) to rotate.

7. The respirator system of claim 6, wherein both the first protrusion (202) and the second protrusion (3011) are strip members; the first protrusion (202) is horizontal when the connection device (200) is in the rest position; the first protrusion (202) is vertical when the connection device (200) is in the connection position.

8. The respirator system of claim 6, wherein a notch that is recessed and penetrates downward to the bottom surface of the humidifier (300) is formed in the second side; the notch comprises a top wall and two opposite side walls, and the second port (30) is formed on the top wall of the notch; the second protrusion (3011) is formed on the two side walls and extend from top to bottom.

9. The respirator system of claim 2, wherein the connection device comprises a main body part and connecting end faces at the two ends of the main body part; a rotating shaft extending along the first side of the host machine of respirator is provided between the two connecting end faces; a shaft hole fit with the rotating shaft is formed in the first side.

10. The respirator system of claim 9, wherein a first slot is formed recessed in the first side; the first slot comprises a bottom wall and four side walls, and the first connect port (10) is formed in the bottom wall of the first slot; the shaft hole (1011) is formed in the side walls of the first slot at the two sides of the first connect port (10).

11. The respirator system of claim 10, wherein a second slot (1010) recessed with respect to the first slot is formed in the first side; when the connection device (200) is in the rest position, a part of the airflow channel extends out of the second slot (1010) and the second port faces downward, and the other part of the airflow channel is accommodated in the second slot (1010).

12. The respirator system of claim 9, wherein the airflow channel comprises a first pipe (2011) for outlet air and a second pipe (2012) for inlet air.

13. The respirator system of claim 12, wherein the first pipe (2011) and the second pipe (2012) are aligned side by side in the axial direction of the rotating shaft (201) and both of them are curved pipes extending along a circumference centering on the rotating shaft (201) as a center line.

14. The respirator system of claim 1, wherein one or more of the first port, the second port, the first connect port and the second connect port is an elastic connect port.

15. The respirator system of claim 1, wherein a linear sealing or face sealing or resilient sealing is formed between the first port and the first connect port or between the second port and the second connect port.

\* \* \* \* \*